United States Patent
Huang et al.

(10) Patent No.: US 9,163,290 B2
(45) Date of Patent: Oct. 20, 2015

(54) METHODS FOR DETECTING HEPATITIS B VIRUS SURFACE GENE NON-SENSE MUTATIONS

(71) Applicant: NATIONAL HEALTH RESEARCH INSTITUTES, Miaoli County (TW)

(72) Inventors: Shiu-Feng Huang, Miaoli County (TW); Chau-Ting Yeh, Taoyuan County (TW); Ya-Ting Chen, Miaoli County (TW)

(73) Assignee: NATIONAL HEALTH RESEARCH INSTITUTES, Miaoli County (TW)

( * ) Notice: Subject to any disclaimer, the term of this patent is extended or adjusted under 35 U.S.C. 154(b) by 174 days.

(21) Appl. No.: 13/912,114

(22) Filed: Jun. 6, 2013

(65) Prior Publication Data

US 2014/0051065 A1   Feb. 20, 2014

Related U.S. Application Data

(60) Provisional application No. 61/684,766, filed on Aug. 19, 2012.

(51) Int. Cl.
| | |
|---|---|
| *C12Q 1/68* | (2006.01) |
| *C07H 21/02* | (2006.01) |
| *C07H 21/04* | (2006.01) |
| *C12Q 1/70* | (2006.01) |
| *G01N 33/569* | (2006.01) |
| *C12P 19/34* | (2006.01) |

(52) U.S. Cl.
CPC .......... *C12Q 1/706* (2013.01); *G01N 33/56983* (2013.01); *C12Q 2600/156* (2013.01)

(58) Field of Classification Search
CPC ............. C12Q 1/706; C12Q 2600/156; G01N 33/56983
See application file for complete search history.

(56) References Cited

U.S. PATENT DOCUMENTS

2008/0160510 A1   7/2008   Inoue et al.

FOREIGN PATENT DOCUMENTS

WO   2004/031729   4/2004

OTHER PUBLICATIONS

Hauss, O. et al., Meth. Mol. Biol., vol. 375, pp. 151-164 (2007).*
Lai MW, Lin TY, Tsao KC, Huang CG, Hsiao MJ, Liang KH, Yeh CT. (2012) Increased Seroprevalence of HBV DNA With Mutations in the S Gene about Individuals >18 Years of Age After Complete Vaccination. Gastroenterology, Augg;143(2):400-7.
Lai MW, Yeh CS, Yeh CT. (2010) Infection with hepatitis B virus carrying novel pre-S/S gene mutations in female siblings vaccinated at birth: two case reports. Journal of Medical Case Reports, 4:190, p. 1-5.
Lee SA, Kim K, Kim H, Kim BJ, (2012) Nucleotide change of codon 182 in the surface gene of hepatitis B virus genotype C leading to truncated surface protein is associated with progression of liver diseases. Journal of Hepatology, vol. 56, 63-69.
Lai W, Huang SF, Hsu CW, Chang MH, Liaw YF, Yeh CT. (2009) Identification of nonsense mutations in hepatitis B virus S gene in patients with hepatocellular carcinoma developed after lamivudine therapy, Antivir Ther.; 14(2):249-61.

* cited by examiner

*Primary Examiner* — Teresa E Strzelecka
(74) *Attorney, Agent, or Firm* — Hsiu-Ming Saunders; Intellectual Property Connections Inc.

(57) ABSTRACT

A method for in vitro detection of the presence of a C-terminal truncation mutation of a hepatitis B virus (HBV) surface (S) gene encoding a small S protein in an isolated nucleic acid sample is disclosed. An in vitro diagnostic kit for use in the aforementioned method is also disclosed.

13 Claims, 5 Drawing Sheets

FIG. 1

```
atggagaacatcgcatcaggactcctaggacccctgctcgtgttacaggcggggttttc     60
 M  E  N  I  A  S  G  L  L  G  P  L  L  V  L  Q  A  G  F  F    20 ttgttgacaaaaatcctcacaataccacagagtctagactcgtggtggacttctctcaat   120
 L  L  T  K  I  L  T  I  P  Q  S  L  D  S  W  W  T  S  L  N    40 tttctaggggaacacccgtgtgtcttggccaaaattcgcagtcccaaatctccagtcac    180
 F  L  G  G  T  P  V  C  L  G  Q  N  S  Q  S  Q  I  S  S  H    60 tcaccaacctgttgtcctccaatttgtcctggttatcgctggatgtgtctgcggcgtttt   240
 S  P  T  C  C  P  P  I  C  P  G  Y  R  W  C  L  R  R  F       80
                                           ↓
atcatcttcctctgcatcctgctgctatgcctcatcttcttgttggttcttctggactat   300
 I  I  F  L  C  I  L  L  C  L  I  F  L  V  L  L  D  Y         100
                                        L95 caaggtatgttgcccgtttgtcctctaattccaggatcatcaacaaccagcaccggacca   360
 Q  G  M  L  P  V  C  P  L  I  P  G  S  S  T  T  S  T  G  P   120 tgcaaaacctgcacaactcctgctcaaggaacctctatgtttccctcatgttgctgtaca   420
 C  K  T  C  T  T  P  A  Q  G  T  S  M  F  P  S  C  C  C  T   140 aaacctacggacggaaactgcacctgtattcccatcccatcatcttgggctttcgcaaaa   480
 K  P  T  D  G  N  C  T  C  I  P  I  P  S  S  W  A  F  A  K   160 tacctatgggagtgggcctcagtccgtttctcttggctcagtttactagtgccatttgtt   540
 Y  L  W  E  W  A  S  V  R  F  S  W  L  S  L  L  V  P  F  V   180
 ↓
cagtggttcgtagggctttcccccactgtctggctttcagttatatggatgatgtggtat   600
 Q  W  F  V  G  L  S  P  T  V  W  L  S  V  I  W  M  M  W  Y   200
   W182                                      ↓
tgggggccaagtctgtacaacatcttgagtccctttatgccgctgttaccaattttcttt   660
 W  G  P  S  L  Y  N  I  L  S  P  F  M  P  L  L  P  I  F  F   220
                                           L216
tgtctttgggtatacatttga                                          681
 C  L  W  V  Y  I  *
```

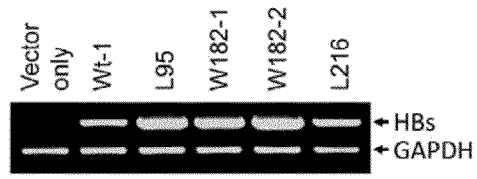
FIG. 7A RNA expression of HBS gene in stable clones
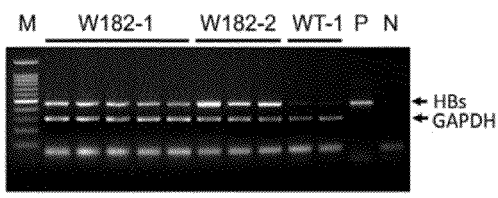
FIG. 7B RNA expression of HBS gene in nude mice tumors
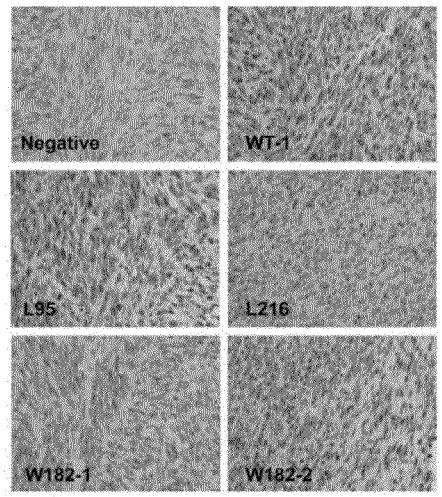
FIG. 7C HBsAg expression of xenograft by IHC stain
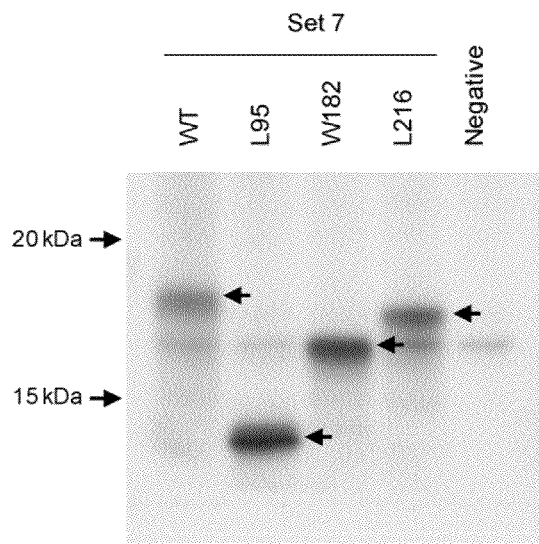
FIG. 8
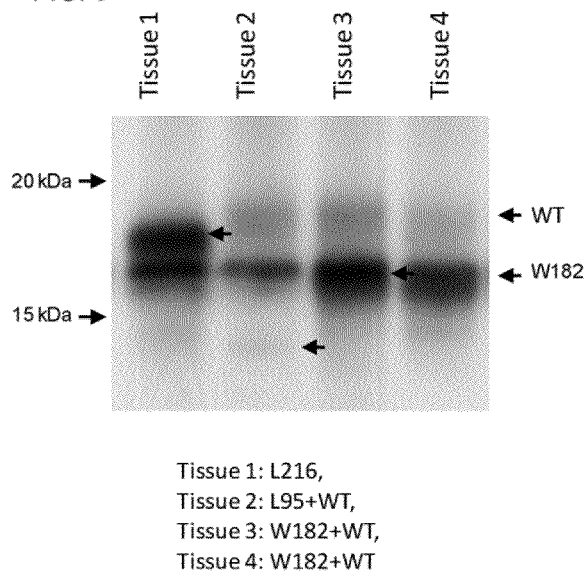
FIG. 9
Tissue 1: L216,
Tissue 2: L95+WT,
Tissue 3: W182+WT,
Tissue 4: W182+WT

METHODS FOR DETECTING HEPATITIS B VIRUS SURFACE GENE NON-SENSE MUTATIONS

REFERENCE TO RELATED APPLICATION

The present application claims the priority to U.S. Provisional Application Ser. No. 61/684,766, filed Aug. 19, 2012, which is herein incorporated by reference in its entirety.

FIELD OF THE INVENTION

The present invention relates generally to hepatocellular carcinoma, and more specifically to hepatitis B virus-related hepatocellular carcinoma.

BACKGROUND OF THE INVENTION

Gene S of hepatitis B virus (EBV) is the gene that codes for the surface antigen (HBsAg). The HBsAg gene is one long open reading frame but contains three in frame "start" (ATG) codons that divide the gene into three sections, pre-S1, pre-S2, and S. Because of the multiple start codons, polypeptides of three different sizes called large S, middle S, and small S (pre-S1+pre-S2+S, pre-S2+S, and S, respectively) are produced. During the course of chronic hepatitis B infection, the viral genome would frequently develop mutations. These mutations represent the attempt of the virus to escape from host immune-surveillance.

Hepatocarcinogenesis of HBV-related HCC is believed to be a "hit-and-run" event as most of the surgically removed cancerous HCC tissues contain rare, if any, freely replicative viruses. Therefore, if certain viral mutations were assumed to be responsible for initiation of the oncogenic process, one could not identify them because the mutant viruses should have been lost in the subsequent steps of hepatocarcinogenesis.

SUMMARY OF THE INVENTION

In one aspect, the invention relates to a method for in vitro detection of the presence of a C-terminal truncation mutation of a hepatitis B virus (HBV) surface (S) gene encoding a small S protein in an isolated nucleic acid sample, comprising:

a) providing a first set of primer pair and a second set of primer pair, the first set of primer pair comprising a first forward primer and a reverse primer, the second set of primer pair comprising a second forward primer and the reverse primer, wherein (i) the first forward primer comprises a nucleotide sequence for annealing to the 5'-end of the S gene and is labeled with a FLAG tag sequence at the 5'-end thereof, the reverse primer has a characteristic of annealing to the 3'-end sequence of the S gene, and the first set of primer pair have characteristics of generating a first polymerase chain reaction (PCR) product, the first PCR product comprising the FLAG tag sequence at the 5'-end thereof;

(ii) the second forward primer comprises, in the 5'→3' direction, a T7 or an Sp6 promoter sequence, a Kozak sequence and a 3'-end sequence that has characteristics of annealing to the FLAG tag sequence located at the 5'-end of the first PCR product, and the second set of primer pair have characteristics of generating a second PCR product comprising the T7 or the Sp6 promoter sequence at the 5'-end thereof, the Kozak sequence, and the FLAG tag sequence, in which the Kozak sequence is located between the T7 or the Sp6 promoter sequence and the FLAG tag sequence;

b) performing a first PCR in a first reaction mixture comprising the isolated nucleic acid sample and the first set of primer pair to generate the first PCR product, wherein the isolated nucleic acid sample is from an HBV carrier or a suspect of HBV carrier;

c) performing a second PCR in a second reaction mixture comprising the first PCR product and the second set of primer pair to generate the second PCR product;

d) translating the second PCR product into a protein;

e) comparing the size of the protein with the size of a control or wild-type small S protein; and f) determining that the C-terminal truncation mutation of the hepatitis B virus S gene is present in the nucleic acid sample when there is a decrease in the size of the protein as compared with the control or the wild type small S protein.

In another aspect, the invention relates to a method for in vitro detection of at least one C-terminal truncation mutation of a hepatitis B virus (HBV) surface (S) gene in a nucleic acid sample, comprising:

a) providing a first forward primer and a reverse primer, the first forward primer comprising a sequence for annealing to the 5'-end of the S gene and having a FLAG tag sequence at the 5'-end thereof, the reverse primer comprising a nucleotide sequence for annealing to the 3'-end of the S gene;

b) performing a first polymerase chain reaction (PCR) in a first reaction mixture comprising the nucleic acid sample, the first forward primer, and the reverse primer to generate a first PCR product, the first PCR product comprising the FLAG tag sequence at the 5'-end thereof, wherein the nucleic acid sample is from a human subject who is a carrier of HBV or a suspect of HBV carrier;

c) providing a second forward primer and the reverse primer, the second forward primer comprising, in the 5'→3' direction, a T7 or a Sp6 promoter sequence, a Kozak sequence with a spacer and a 3'-end sequence that has a Characteristic of annealing to the FLAG tag sequence at the 5'-end of the first PCR product;

d) performing, a second PCR in a second reaction mixture comprising the first PCR product, the second forward primer, and the reverse primer to generate a second PCR product, the second PCR product comprising the T7 or the Sp6 promoter sequence at the 5'-end thereof the Kozak sequence, the FLAG tag sequence, the Kozak sequence being located between the T7 or the Sp6 promoter sequence and the FLAG tag sequence;

e) translating the second PCR product into a protein; and f) comparing the size of the second PCR product with the size of a wild-type small S protein; and (g) determining that the C-terminal truncation mutation of the hepatitis B virus S gene is present in the nucleic acid sample when the size of the protein is smaller than that of the wild-type small S protein.

Further in another aspect, the invention relates to an in vitro diagnostic kit for use in detecting the presence of a C-terminal truncation mutation of a hepatitis B virus (HBV) surface (S) gene in a nucleic acid sample, comprising:

(a) a first set of primer pair, which have characteristics of annealing to the HBV S gene in the nucleic acid sample in a first polymerase chain reaction (PCR) for generating a first polymerase chain reaction (PCR) product, the first PCR product spanning the sequence of the HBV S gene for encoding a small S protein at least from the amino acid position 123 to the amino acid position 227 of SEQ ID NO: 2 and is labeled with a FLAG tag sequence at the 5'-end thereof; and (b) a second set of primer pair, which have characteristics of annealing to the first PCR product in a second PCR for generating a second PCR product, the second PCR product spanning the sequence of the first PCR product and comprising a T7 or a Sp6 promoter sequence at the 5'-end thereof, a Kozak sequence, and the FLAG tag sequence, the Kozak sequence being located between the T7 or the Sp6 promoter sequence and the FLAG tag sequence.

In one embodiment of the invention, the C-terminal truncation mutation of the HBV S gene is selected from the group consisting of sL15*, sL21*, sS61*, sC69*, sL95*, sW156*, sW163*, sW172*, sW182*, sW196*, and sL216*.

In another embodiment of the invention, the comparing step is performed by a Western blot or chemiluminescent detection system.

In another embodiment of the invention, the nucleic acid sample is obtained from a patient who is suspected of having a hepatitis B virus (HBV) infection or hepatocellular carcinoma, or has an abnormal liver function or has liver cirrhosis.

In another embodiment of the invention, the nucleic acid sample is extracted from a fresh frozen liver tissue or a formalin-fixed paraffin tissue section, or a blood sample.

In another embodiment of the invention, the first PCR product spans the sequence of the HBV S gene for encoding, the small S protein at least from the amino acid position 123 to the amino acid position 227 of SEQ ID NO: 2 and is labeled with a FLAG tat sequence at the 5'-end thereof.

In another embodiment of the invention, the first PCR product spans the sequence of the HBV S gene encoding the small S protein from the amino acid position 30 to the amino acid position 227 of SEQ ID NO: 2, or from the amino acid position 123 to the amino acid position 227 of SEQ ID NO: 2.

In another embodiment of the invention, the Kozak consensus sequence is SEQ ID NO: 5 or SEQ ID NO: 6.

In another embodiment of the invention, the first set of primer pair in the aforementioned in vitro diagnostic kit comprises a first forward primer and a reverse primer the second set of primer pair comprises a second forward primer and the reverse primer, and wherein (i) the first forward primer comprises a FLAG tag sequence at the 5'-end thereof; and (ii) the second forward primer comprises, in the 5'→3' direction, the T7 or the Sp6 promoter sequence, the Kozak sequence and a 3'-end sequence that has a characteristic of annealing to the FLAG tag sequence at the 5'-end of the first PCR product.

In another embodiment of the invention, the aforementioned primers are as follows:

a) the first forward primer of the first set of primer pair comprises a nucleotide sequence selected from the group consisting of SEQ ID NOs: 8, 11, 13, 14, and 16;

b) the second forward primer of the second set of primer pair comprises a nucleotide sequence selected from the group consisting of SEQ ID NOs: 10, 12, 15 and 17; and c) the reverse primer comprises the nucleotide sequence of SEQ ID NO: 9.

In another embodiment of the invention, the first forward primer and the second forward primer comprise nucleotide sequences respectively selected from the group consisting of:

(a) SEQ ID NOs: 8 and 10;
(b) SEQ ID NOs: 11 and 12;
(c) SEQ ID NOs: 8 and 12;
(d) SEQ ID NOs: 13 and 12;
(e) SEQ ID NOs: 13 and 10;
(f) SEQ ID NOs: 14 and 12;
(g) SEQ ID NOs: 14 and 15;
(h) SEQ ID NOs: 14 and 10; and
(i) SEQ ID NOs: 16 and 17.

Further in another embodiment of the invention, the sequence of the first forward primer is SEQ ID NOs: 14, and the sequence of the second forward primer is SEQ ID NO: 15.

Yet in another embodiment of the invention, the aforementioned primers are as follows:

a) the first forward primer of the first set of primer pair consists of a nucleotide sequence selected from the group consisting of SEQ ID NOs: 8, 11, 13, 14, and 16;

b) the second forward primer of the second set of primer pair consists of a nucleotide sequence selected from the group consisting of SEQ ID NOs: 10, 12, 15 and 17; and c) the reverse primer consists of the nucleotide sequence of SEQ ID NO: 9.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 1 shows the HBV S gene sequence SEQ ID NO: 1 and its protein (small S) sequence SEQ ID NO. 2.

FIG. 7A shows m-RNA expression of HBV S gene was all positive in the 5 stable clones of HBV S gene, including wild type (WT), and the 3 truncation mutants: L95, L216, W182-1 and W182-2.

FIG. 7B shows that the tumors of xenograft study from WT and two W182 stable clones all had m-RNA expression of HBV S gene.

FIG. 7C shows that tumors in xenograft study from WT and the 3 HBS truncation mutants all had HBS protein expression by immunohistochemical (IHC) staining (IHC stain for HBsAg, 100×).

FIG. 8 Application on three different HBV C-terminal truncation mutants. The results of detection by transcend chemiluminescent detection system are shown. The signals were strong and the protein sizes of all 3 mutants are all correct.

FIG. 9 Application on the HCC tissue samples (500 ng) of 4 HBV patients with transcend chemiluminescent detection system are shown. Different truncation mutations were identified successfully. The intensity was directly correlated with the amount of mutant clones in the tissue.

DETAILED DESCRIPTION OF THE INVENTION

Definitions

Figure 2:
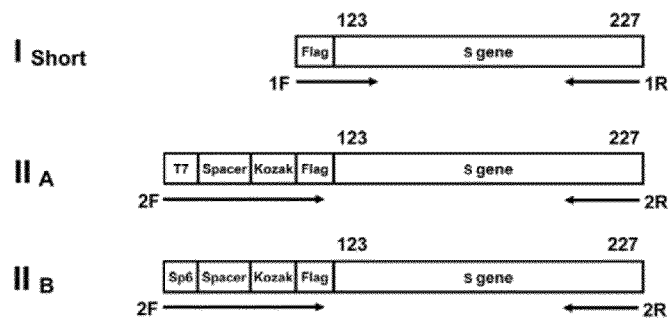
FIG. 2 illustrate the design of a first pair of primers (1F and 1R) and a second pair of primers (2F and 2R). In the first pair of primers (1F and 1R), the forward primers (1F) illustrated here is a short form type. In the second pair of primers (2F and 2R), the forward primer may contain a T7 promoter or a S6 promoter. The 1R and 2R are the same (i.e., having identical sequence).

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of as term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of an exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

Large S protein is encoded by the large S gene, which includes preS1, PreS2 and S gene. The gene sequence for the small S protein is called S gene, the other two are called Pre S1 gene and PreS2 gene (encoding the large S and Middle S proteins).

The terms "Kozak consensus sequence", "Kozak consensus" and "Kozak sequence" are interchangeable.

T7 RNA polymerase is an RNA polymerase from the T7 bacteriophage that catalyzes the formation of RNA in the 5'→3' direction, T7 polymerase is extremely promoter-specific and transcribes only DNA downstream of a T7 promoter. The T7 polymerase also requires a DNA template and $Mg^{2+}$ ion as cofactor for the synthesis of RNA.

Sp6 RNA polymerase is an RNA polymerase from the Sp6 bacteriophage that catalyzes the formation of RNA in the 3' direction. Sp6 polymerase is extremely promoter-specific and transcribes only DNA downstream of a Sp6 promoter. The Sp6 polymerase also requires a DNA template and $Mg^{23+}$ ion as cofactor for the synthesis of RNA.

The term "5'-end" of a primer or a PC R product shall generally mean 5'-terminal portion of the primer or 5'-terminal portion of the PCR product.

A nonsense mutation is a point mutation in the sequence of DNA that results in a premature stop codon, or a nonsense colon in the transcribed mRNA, the consequence of which is early termination of the translation of protein. This kind of protein is called C-terminal truncation protein, and the DNA mutation is called C-terminal truncation mutation. The C-terminal truncated protein is usually unstable.

The terms "L95" and "sL95*" are interchangeable; the terms "W182" and "sW182*" are interchangeable; the terms "L216" and "sL216*" are interchangeable.

The invention relates to detection of HBV S gene mutations in association with HCC. It was discovered that S gene C-terminal truncation mutants (sW182*, sL95*, and sL216*) derived from freely replicative viruses in HCC tissues all possessed oncogenic activity. The invention relates to the discovery of proteins involved in HBV-related oncogenesis. The nucleotide sequence of the S gene of HBV is listed in SEQ ID NO: 1 (S gene sequence from accession No. AY167089). The amino acid sequence of HBV small S protein is listed in SEQ ID NO: 2 (see FIG. 1).

Examples of HBV S gene C-terminal truncation mutations:

sL15* represents a point mutation of the S gene, resulting in a stop codon at the amino acid position L15 of the small S protein.

sL21* represents a point mutation of the S gene, resulting in a stop codon at the amino acid position L21 of the small S protein.

sS61* represents nucleotide 182 C to G or C to A substitution of the S gene (SEQ ID NO: 1), resulting in a stop codon at the amino acid position S61 of the small S protein (SEQ ID NO: 2).

sC69* represents nucleotide 207 T to A substitution of the S gene, resulting in a stop codon at amino acid position C69 of the small S protein.

sL95* is nucleotide 284 T to A substitution of the S gene, resulting in a stop codon at amino acid position L95 of small S protein.

sW156* represents a point mutation of the S gene, resulting in a stop codon at the amino acid position W156 of the small S protein.

sW163* represents a point mutation of the S gene, resulting in a stop codon at the amino acid position W163 of the small S protein.

sW172* represents a point mutation of the S gene, resulting in a stop codon at the amino acid position W172 of the small S protein.

sW182* is nucleotide 546 G to A substitution of the S gene, resulting in a stop codon at amino acid position W182 of the small S protein.

sW196* represents a point mutation of the S gene, resulting in a stop codon at the amino acid position W196 of the small S protein.

sL216* is nucleotide 647 T to A substitution of the S gene, which will cause a stop codon at the amino acid position L216 of the small S protein.

Preparation of DNA Samples from Specimens for Test

All HBV carriers are eligible for the test. HBV carriers with persistent inflammatory activity (abnormal liver function test) or with cirrhosis are the main population with risk of developing HCC. Thus these patients are the main patient population for the test. A patient's DNA sample may be obtained from various sources. For example, DNA may be extracted from the serum or plasma of the patient, or extracted from a fresh frozen liver tissue (biopsy or operative specimen), or from liver tissue dissected from the formalin-fixed paraffin sections. Tissue specimens may be obtained from an operative specimen or biopsy specimen.

Design of Primers

Figure 3:
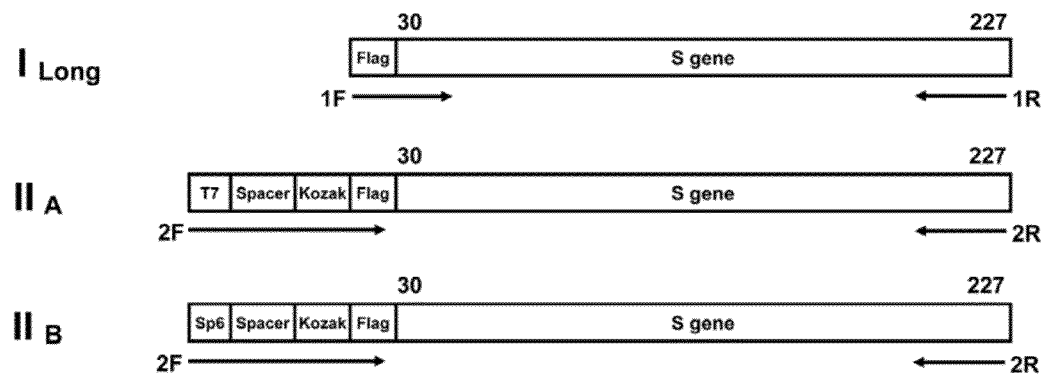
FIG. 3 illustrate the design of a first pair of primers (1F and 1R) and a second pair of primers (2F and 2R). In the first pair of primers, the forward primers 1F is a long form type, and in the second pair of primers, the forward primer (2F) may contain a T7 promoter or a S6 promoter. The 1R and 2R are the same (i.e., having an identical sequence).

FIGS. 2 and 3 show the design of the primers. Two sets (the first set-primer pair and the second set-primer pair) of primer pairs are required to practice the claimed invention. Each set consists of a forward primer and a reverse primer. The reverse primer in the first set-primer pair may be the same as the reverse primer in the second set-primer pair.

The first set-primer pair (including the forward primer 1F and the reverse primer 1R) are designed to span HBV surface gene and the PCR product amplified by the first set primer pair comprise a FLAG sequence at the N-terminal region (or end) of the PCR product.

In addition, the first set-primer pair may be designed to have two types, a short form type ($I_{Short}$) and a long form type ($I_{Long}$). The two types differ in the annealing site of the forward primer, but have the same annealing site for the reverse primer. The PCR product of $I_{Short}$ spans a shorter region of the S gene (e.g., a.a. 123 to a.a. 227) (FIG. 2), while the PCR product of $I_{Long}$ spans a longer region of the S gene (e.g., a.a. 30 to a.a. 227) (FIG. 3).

The second set-primer pair is designed in such that the PCR product amplified by the second set comprise a T7 or an Sp6 promoter, a spacer sequence, and a Kozak sequence at the N-terminal portion of the PCR product. The second set-primer pair may also have two types: IIA and IIB. The PCR product resulted from the second-set primer pair IIA comprises the T7 promoter at the N-terminal portion of the PCR product. The PCR product resulted from the second set-primer pair IIB comprises the Sp6 promoter at the N-terminal portion of the PCR product.

As shown in FIG. 2, the first set primer pair are designed in such that the first PCR product generated would span at least one half of the small S protein's C-terminal (starting from a.a. 123 to a.a. 227) encoding region of the HBV S gene, and have a FLAG sequence at the N-terminal of the first PCR product. To have the first PCR product to span a wider region of the C-terminal of the small S protein in order to catch more truncation mutants, another forward primer of the first set primer pair was designed to have the starting point very close to the N-terminal (starting from a.a. 30 to a.a. 227) of the S protein (FIG. 3). A PCR product resulted from the fast set primer pair (which amplify HBV small S protein-encoding gene in the DNA sample from a patient) is designated as "a first PCR product".

The second set primer pan are designed to generate a second PCR amplicon product that comprises a T7 or an Sp6 promoter at the N-terminal end of the second PCR product. The template used by the second-set primer pair is the first PCR product generated by the aforementioned first set primer pair. A PCR product resulted from the second set primer pair is designated herein as "a second PCR product". The second PCR product is translated into a protein by using a in vitro translation kit. The translated protein may be detected by Western Blot or using a TRANSCEND™ Chemiluminescent Translation detection system.

If the patient has a stop codon mutation in the small S protein-encoding gene (S gene), the translated protein will have a smaller size than the wild type small S protein (control) due to C-terminal truncation. The size of the control (wild type) small S protein is 22.8 kDa.

Neither the first PCR product nor the second PCR product by itself could be used to evaluate whether a small S protein C-terminal truncation mutation was present because there was only one nucleotide mutation in the S gene in the DNA sample. Under this circumstance, the size of the PCR product from a PCR reaction containing a mutant DNA template would remain the same as the size of the PCR product from a PCR reaction containing a wild type (or control) DNA template. However, a mutant of the small S protein is a truncated form and its size is smaller than a wild type S protein. Therefore, the invention relates to methods for evaluation or determination of the presence of a C-terminal truncation mutation by designing two set of primer pairs to allow observation and examination of C-terminal truncated small S protein (i.e., C-terminal truncated mutation of the S gene). The method detects protein truncation (or detects truncated proteins). The test is cost-effective because no sequencing of a PCR product is required. Furthermore, the method eliminates the need for knowing the location of a stop codon.

T7 promoter (TAATACGACTCACTATAGG; SEQ ID NO: 3);

Sp6 promoter (TATTTAGGTGACACTATAG; SEQ ID NO: 4):

The Kozak consensus sequence with a short spacer is GAGCCACCATG (SEQ ID NO: 5); the Kozak consensus sequence with a long spacer is AACAGCCACCATG (SEQ ID NO: 6).

FLAG (GACTATAAAGACGACGACGACAAA; SEQ ID NO: 7).

In vitro translation kit is commercially available such as TNT® Quick Coupled Transcription/Translation System (Promega Corporation, WI, USA.):

PCR Conditions for Amplifying Target DNA.

According to the invention, two PCR reactions were performed. The first PCR reaction was performed in a total volume of 50 µl with 1 µl of a DNA sample. The PCT profile is as follows: initial denaturing at 94° C. for 5 min, followed by 35 cycles of the denaturing step at 94° C. for 30 s, an annealing step at 55° C. for 45 s and an extension step at 72° C. for 1 min, and a final extension step at 72° C. for 7 min. The second PCR reaction was performed by taking 2 µl of the sample at the end of the first PCR reaction using the same profile as the first PCR.

Protein Detection Method:

Western blot procedure and other detection method such as TRANSCEND™ Chemiluminescent detection system are well known in the art and may be used to detect the translated protein. The DNA nucleotide sequence of HBV could be quite different when using different genotypes of HBV as a reference sequence, even though the a.a. sequences are all the same. However, the location of the primers designed is consensus between different genotypes, thus the primers can anneal to different genotypes of HBV DNA template. The size of the protein could be evaluated according to the markers on the membrane.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods

Routine immunohistochemical (IHC) staining of HBsAg (Virostat, ME, Portland) and HBcAg (Dako, CA, USA) were performed from year 2000 to 2002 on HCC liver tissue sections that were surgically removed from patients with HBV infection in Chang-Gung Memorial Hospital (CGMH) for future antiviral treatment. The study protocol was approved by the Institutes of Reviewing Board of Chang-Gang memorial Hospital and National Health Research Institutes. The animal protocol had also been approved by the Institutional Animal Care and Use Committee of National Health Research Institutes.

Identification of HBV Mutations

DNA extraction was performed using Hirt extraction procedure followed by Quiagen DNA extraction (QIAGEN, Hilden, Germany). Direct sequencing of full-length HBV genomes was performed. Forward and reverse sequencing reactions were done with the same primers for PCR amplification and ABI BigDye Terminator kit v3.1 on an ABI3730 genetic analyzer (Applied Biosystems, Foster City, Calif.) according to manufacturer's instructions. Sequence variations were determined by using Seqscape software (Applied Biosystems, Foster City, Calif., USA) with the Hepatitis B virus reference sequence (AY167089 for genotype B and AY167095 for genotype C, National Center for Biotechnology Information).

Transforming Activity of S Gene C-Terminal Truncation Mutants

1. Plasmid Construction and Site Directed Mutagenesis

The wild type (wt) preS/S region of HBV was amplified from pCMV-HBV plasmid, which contained longer-than-one copy of HBV genome (GenBank accession number X02763), using the PreSF and SR primers. The PCR product was inserted into pIRESbleo plasmid (BD Biosciences Clontech, NJ, USA) to generate the construct of pIRES-preS/S-wt (which means the wild type sequence of the large S protein-encoding gene, including PreS1 gene PreS2 gene and S gene). A CMV promoter was used. To construct plasmids encoding truncated large S proteins containing 3 nonsense mutations, sL95*, sW182* and sL216* of S gene, respectively, site directed mutagenesis experiments were preformed according to a PCR-based method. All plasmids were sequence verified using an automatic DNA sequencer (Applied Biosystems, CA, USA).

2. Cell Culture and Plasmid Transfection for Establishment of Stable Clones of Three S Truncation Mutants NIH3T3 cells were maintained in Dulbecco's modified Eagle's medium supplemented with 10% calf serum, 2 mM glutamine, 100 unit/ml penicillin and 100 µg/ml streptomycin. Cells were maintained at 37° C. in a 5% $CO_2$ incubator. Transfection with pIRESbleo plasmids encoding wild type or truncated large S proteins was performed using Lipofectamine 2000 reagent (Invitrogen, CA, USA).

3. Transformation and Tumorigenesis Assays

I. Cell Proliferation Assays

The WST-1 reagent was used for cell proliferation assay. It was diluted (1:10) in culture media. One thousand cells (from the four NIH3T3 stable cell lines: the Mock, Wt, sL95*, sL216*, and sW182*) were seeded in each well of a 96-well culture plate, and incubated for 12 hours. After cell attachment, the culture media were changed to the media with no sera, then incubated for 24 hours for synchronization. After Day 0 data were collected, culture media were changed back to complete media and renewed every two days. After 4 hours incubation, the optical densities of wave length 450 nm were read. Each detecting point was analyzed in 5 independent experiments. The growth curves were calculated as the ratios of absorbance readings in Day N to that in Day 0 of the tested stable clones II. Cell Anchorage Independence Abilities The cell anchorage independence assays were performed in 6-well plates. The bottom layer was 1.5 ml 0.7% agarose (SeaPlaque) with complete culture media. The upper layer was 2 ml 0.5% agarose mixed with complete culture media and 5000 cells (from the four NIH3T3 stable cell lines: the Mock, Wt, sL95*, sL216*, and sW182*). The top layer was 1 ml complete culture medium and refreshed every 2 days. Colonies were visualized by 0.1% p-iodonitro tetrazolium violet (INT) staining. Each stable clone experiment was performed in triplicate and 3 randomly selected fields for each well was subjected for colony number calculation in the same objective magnification (20×). The colony number was counted by the soft ImageJ (NIH).

III. The Xenograft Assays for Tumorigenicity

Male BALB/c mice were obtained from the National Animal Experimental Center (Taipei, Taiwan). The mice were maintained in specific pathogen-free conditions. Four-week-old athymic mice (4-5 per group) were injected subcutaneously with $1 \times 10^6$ cells (from the four NIH3T3 stable cell lines: the Mock, Wt, sL95*, sL216*, and sW182*). Tumor growth was monitored and measured weekly until week 13. The mice were then sacrificed. If there was tumor growth, the tumor and liver were excised, formalin-fixed and paraffin-embedded for histopathology examination. Portions of the tumor and liver tissue were frozen for DNA, RNA and protein extraction. If there was no tumor growth grossly, the skin and its subcutaneous tissue of the injection site were excised for histopathology confirmation.

Results

Figure 4A:
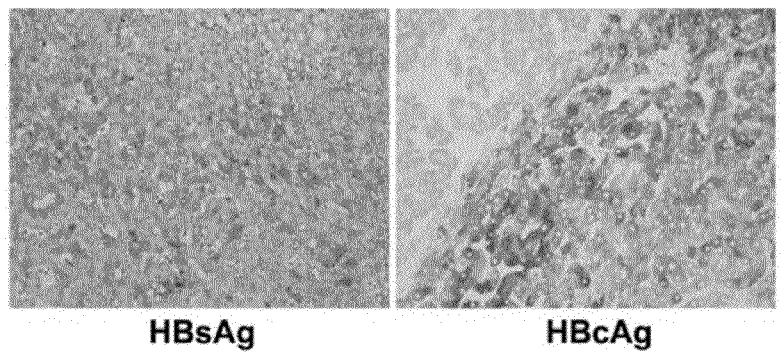
FIGS. 4A-B shows hepatitis B viruses (HBV) identified in the hepatocellular carcinoma (HCC) tumor tissue. A. Diffusely positive staining of hepatitis B surface antigen (HBsAg) and hepatitis B core antigen (HBcAg) in one HBcAg(+) HCC tissue section (immunohistochemical staining, 100×). B. Southern blot analyses of 19 HBcAg(+) HCC tumor tissues revealed abundant single-strand (SS) form and relaxed-circular (RC) forms of HBV DNA, consistent with presence of freely replicative viruses. HepG2-HBV was used as positive control. T: tumor liver tissue. N: non-tumor liver tissue. Samples obtained from different patients were labeled by Arabic numbers as indicated.
Figure 4B:
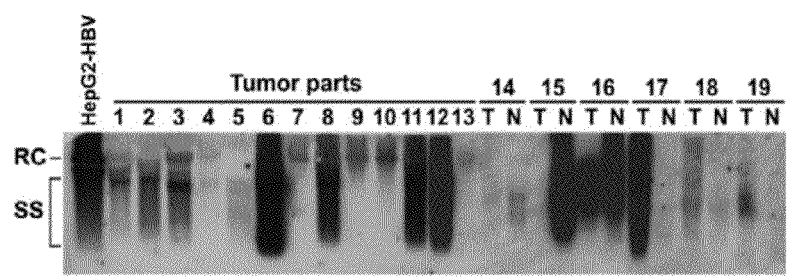

From year 2000 to 2002, we have performed immunohistochemistry stains on 300 HBV-related surgically removed HCC specimens in Chang-Clung Memorial Hospital and identified 28 HCC tissues which were positive for hepatitis B core antigen (HBcAg) expression in the cancerous parts, suggesting that HBV might still be viable in the HCC tissue. Among 300 HCC liver tissue sections analyzed by the IHC staining, 106 tumor tissues (353%) were positive for HBsAg, and only 28 tumors (9.3%) were positive for HBcAg (FIG. 4A). Among them, 25 HBcAg-positive HCC patients in cancerous parts had available fresh frozen tumor tissues and paired benign liver tissue in the tumor bank of CGMH for further studies. A total of 19 of the 25 HBcAg-positive tumors had sufficient amount of DNA samples (>100 µg) for Southern blot analyses (FIG. 4B). The data demonstrated that abundant single-strand (SS) form and relaxed-circular (RC) forms of HBV, which is consistent with the presence of freely replicative HBV viruses. The SS and RC forms were identified and isolated from the HBcAg-positive HCC tissues in all of the 19 patients. HepG2-HBV was used as positive control. T: tumor tissue, N: non-tumor liver tissue.

Clinicopathological Characteristics of HCC Patients with HBcAg-Positive HCC Tissues To understand the clinical significance of positive HBcAg in HCC tissue, we have compared the clinicopathological characteristics of the 25 HBcAg-positive HCC patients with 25 gender and age-matched HBcAg-negative HCC patients operated in the same time period. HBcAg-positive HCC patients were significantly associated with cirrhosis ($p<0.001$), and small tumor size ($\leq 2$ cm) ($p=0.039$). The median disease free survival (DFS) and overall survival (OS) for HBcAg-positive HCC patients (21.2 months and 72.2 months, respectively) were all longer than HBcAg-negative patients (9.8 months and 44.0 months, respectively), but both were statistically non-significant ($P=0.686$ and $0.793$, respectively).

Identification of Viral Mutations Associated with Cancerous HCC Tissues by Whole Genome HBV DNA Sequence Analyses Whole genome HBV DNA sequencing was performed on all of the 25 pairs of HBcAg-positive HCCs, including the cancerous and noncancerous parts. All of the four HBV genes (S, C, X and P) were successfully sequenced in the HBcAg-positive HCC tumor tissue. The complete HBV sequence data of the 25 HBcAg-positive HCC tumor and paired non-tumor tissue had been uploaded on NCBI Nucleotide database (EU487256-EU487257, EU522066-EU522075, EU564820-EU564826, EU660224-EU660233, EU881995-EU882006, EU919161-EU919176) in year 2008, and released in years 2009 and 2010. All mutations found in this study were heterolozygous, since wild type was always co-existing (the sequence data showed coexisting of different sequences in the same region). Three premature stop codon mutations of S gene were identified in the cancerous part of 4 tumors (sL95*, sW182* in two tumors, and sL216*), while only one mutation (sW182*) was found in the paired benign tissue.

Additional sequencing of whole HBV genome of the 25 gender and age-matched HBcAg-negative HCCs were performed. There were totally 12 mutations in the cancerous pans, and only 3 in the paired non-cancerous parts ($p=0.004$), sW182* was repeatedly identified, being found in 6 of the 50 tumors.

To understand the frequency of sW182* in HCC, we did more sequence analyses of the HBV S gene in HBV-related HBcAg-negative HCCs. Additional 55 HCC tumor tissue and paired benign liver tissues were examined, but only 33 HCC tumor tissues and 46 benign liver tissues were successful in sequencing. Additional 6 HBV S premature stop codon mutations were found in tumors, which include 3 tumors with sW182*, but none in the benign liver tissue. Among the 9 tumors with sW182* mutations, five of them also had other S truncation mutations. Functional studies of the 3 truncation mutations (sL95*, sW182* and sL216*) found in the 25 HBcAg-positive HCCs were performed.

Transformation and Tumorigenesis Assays

1) Cell Proliferation Assays

Figure 5A:
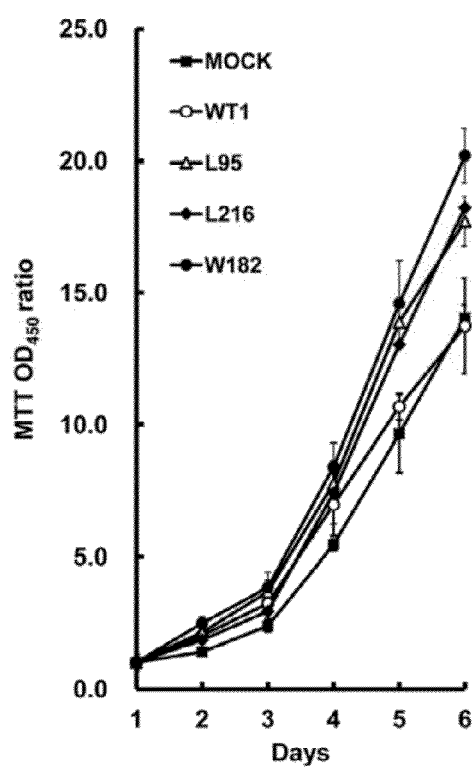
FIGS. 5A-C show functional studies of three HBs mutants (L98, W182 and L216) compared with wild type (WT). A. Cell proliferation assay revealed, that all three HBs mutants could enhance the host cell growth. B. Cell anchorage independence ability study revealed that W182 had the highest colony counts. C. Wild type and three mutants all had significantly higher colony counts than Mock. Mock stands for a negative control group.

The proliferation assay of the 4 stable clones: wild type (WT), L95, W182 and L216, indicated that all three S truncation mutants could enhance the cell growth compared with Wt and Mock (FIG. 5A).

2) Cell Anchorage Independence Abilities

Figure 5B:
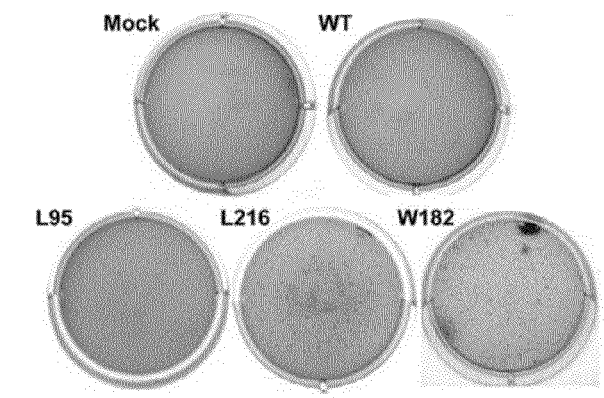
Figure 5C:
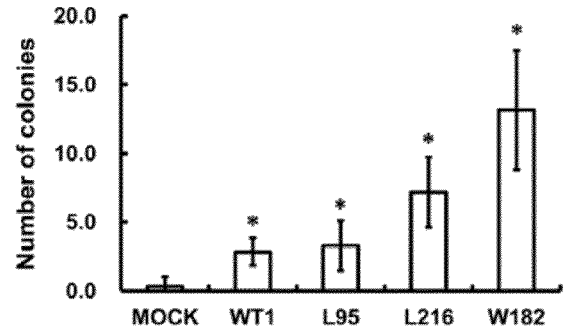

Colonies of 4 stable cell clones: the Mock, WT, L95, L216, and W182, in soft agar were visualized by 0.1% p-iodonitro tetrazolium violet (INT) staining. The average colony numbers counted by the Soft ImageJ (NIH) were shown (FIG. 5B). Wt and three mutants all had significantly higher colony counts than Mock. Among the three mutants. W182 had the highest colony counts (FIG. 5C).

3) The Xenograft Study

Figure 6A:
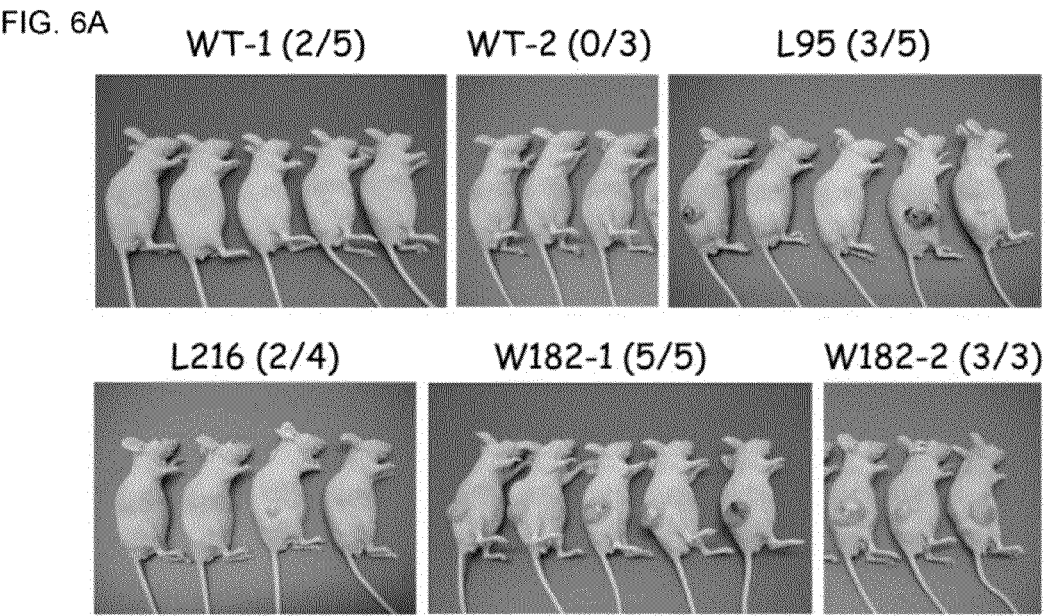
FIGS. 6A-B show the results of a nude mice xenograft study by subcutaneous injection of the cells from the stable clones, which included 3 HBV S truncation mutants (L95, W182-1, W182-2 and L216), wild type (WT-1, WT-2), and Mock (stands for the negative control group). A. The W182 mutant showed the highest incidence (100%) of tumor occurrence and largest tumor sizes. B. Only W182 mutant had statistically significant higher tumor growth rate compared with Mock.
Figure 6B:
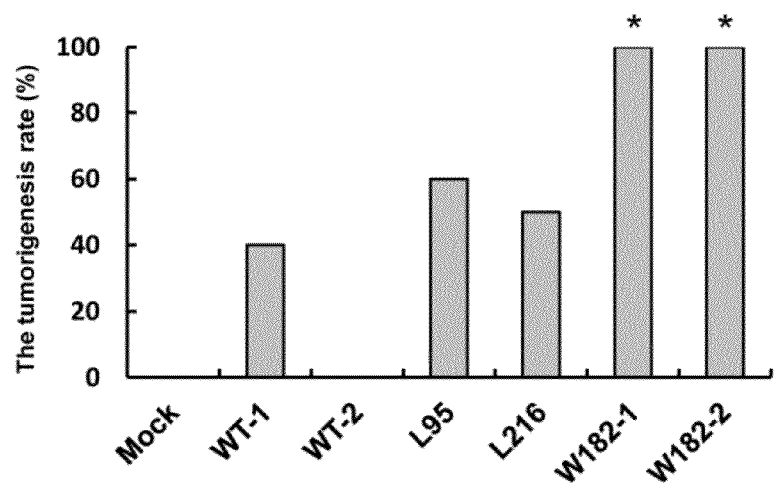

Xenograft studies were performed using 4 weeks old male athymic. BALB/c nude mice with subcutaneous injection of $1\times10^6$ pIRES-preS/S-wt and pIRES-preS/S-mut stable clone cells, which included Mock, WT-1, WT-2, and three HBV S truncation mutants: L95, L216, W182-1, and W182-2 at the same time. Tumor growth was monitored and measured weekly until week 13. Wt and all three mutants had tumor growth in some or all mice. Only the W182-1 (100%) and W182-2 clones (100%) had significant higher tumor growth rate compared with Mock, and the tumor sizes of W182 clones were also the largest compared with Wt and the other two mutants (FIGS. 6A and 6B). The RNA expression of HBS gene was all positive in the stable clones except Mock and the tumors of xenograft study (FIGS. 7A and 7B). Immunohistochemical (IHC) stains of the tumor tissues from the nude mice xenograft study all had HBS protein expression, too (FIG. 7C). Among the tumors, expression of HBS protein was lowest in L216 mutant by IHC stains, which somewhat correlated with the tumor sizes, since L216 had the smallest tumors (FIG. 6A)

Detection of Non-Sense Mutations (C-Terminal Truncation Mutants) of HBV S Gene by In Vitro Translation.

We have identified a series of HBV surface (S) gene non-sense mutations that were significantly associated with HCC, and these mutations also have been confirmed to be carcinogenic by animal studies. The above results suggested that HBV S gene nonsense mutations could be a predicting factor for HCC. Since there are multiple HBV S gene non-sense mutations, and they could co-exist in a tumor, we have developed a technique that use specific primer sets to detect HBV S gene non-sense mutations by in vitro translation, instead of direct sequencing of mutations one by one, in total, we have designed 9 sets of primer pairs for detection of non-sense mutations (C-terminal truncation mutants) of HBV S gene by in vitro translation. These primer pairs for detection of HBV S gene non-sense mutations are shown in Table 1. According to the invention, to test for the presence of truncated mutants, two sets of primer pairs are required, each of which consists of a forward primer and a reverse primer (e.g., in Table 1, the first set primer pair consists of 1F and 1R the second set primer pair consists of 2F and 2R).

TABLE 1

| E.g. | 1st set- & 2nd set-primer pairs | Primer sequence |
|---|---|---|
| 1 | 1-1F | ATGGACTATAAAGACGACGACGACAAAACCTGCACGACTC CTGCTCAA (SEQ ID NO: 8) |
| | 1-1R | TTAAATGTATACCCAAAGACAAAAG (SEQ ID NO: 9) |

TABLE 1-continued

| E.g. | 1st set- & 2nd set-primer pairs | Primer sequence |
|---|---|---|
| | 1-2F | GGATCCTAATACGACTCACTATAGGGAGCCACCATGGACTA TAAAGACGACGAC (SEQ ID NO: 10) |
| | 1-2R | TTAAATGTATACCCAAAGACAAAAG (SEQ ID NO: 9) |
| 2 | 2-1F | CCATGGACTATAAAGACGACGACGACAAAACCTGCACGAC TCCTGCTCAA (SEQE ID NO: 11) |
| | 2-1R | TTAAATGTATACCCAAAGACAAAAG (SEQ ID NO: 9) |
| | 2-2F | GGATCCTAATACGACTCACTATAGGAACAGCCACCATGGAC TATAAAGACGACG (SEQ ID NO: 12) |
| | 2-2R | TTAAATGTATACCCAAAGACAAAAG (SEQ ID NO: 9) |
| 3 | 3-1F | ATGGACTATAAAGACGACGACGACAAAACCTGCACGACTC CTGCTCAA (SEQ ID NO: 8) |
| | 3-1R | TTAAATGTATACCCAAAGACAAAAG (SEQ ID NO: 9) |
| | 3-2F | GGATCCTAATACGACTCACTATAGGAACAGCCACCATGGAC TATAAAGACGACG (SEQ ID NO: 12) |
| | 3-2R | TTAAATGTATACCCAAAGACAAAAG (SEQ ID NO: 9) |
| 4 | 4-1F | CCATGGACTATAAAGACGACGACGACAAACAGAGTCTAGA CTCGTGGTGG (SEQ ID NO: 13) |
| | 4-1R | TTAAATGTATACCCAAAGACAAAAG (SEQ ID NO: 9) |
| | 4-2F | GGATCCTAATACGACTCACTATAGGAACAGCCACCATGGAC TATAAAGACGACG (SEQ ID NO: 12) |
| | 4-2R | TTAAATGTATACCCAAAGACAAAAG (SEQ ID NO: 9) |
| 5 | 5-1F | CCATGGACTATAAAGACGACGACGACAAACAGAGTCTAGA CTCGTGGTGG (SEQ ID NO: 13) |
| | 5-1R | TTAAATGTATACCCAAAGACAAAAG (SEQ ID NO: 9) |
| | 5-2F | GGATCCTAATACGACTCACTATAGGGAGCCACCATGGACTA TAAAGACGACGAC (SEQ ID NO: 10) |
| | 5-2R | TTAAATGTATACCCAAAGACAAAAG (SEQ ID NO: 9) |
| 6 | 6-1F | GGACTATAAAGACGACGACGACAAACAGAGTCTAGACTCG TGGTGG (SEQ ID NO: 14) |
| | 6-1R | TTAAATGTATACCCAAAGACAAAAG (SEQ ID NO: 9) |
| | 6-2F | GGATCCTAATACGACTCACTATAGGAACAGCCACCATGGAC TATAAAGACGACG (SEQ ID NO: 12) |
| | 6-2R | TTAAATGTATACCCAAAGACAAAG (SEQ ID NO: 9) |
| 7 | 7-1F | GGACTATAAAGACGACGACGACAAACAGAGTCTAGACTCG TGGTGG (SEQ ID NO: 14) |
| | 7-1R | TTAAATGTATACCCAAAGACAAAAG (SEQ ID NO: 9) |
| | 7-2F | GGATCCTATTTAGGTGACACTATAGAACAGACCACCATGGA CTATAAAGACGACG (SEQ ID NO: 15) |
| | 7-2R | TTAAATGTATACCCAAAGACAAAAG (SEQ ID NO: 9) |
| 8 | 8-1F | GGACTATAAAGACGACGACGACAAACAGAGTCTAGACTCG TGGTGG (SEQ ID NO: 14) |
| | 8-1R | TTAAATGTATACCCAAAGACAAAAG (SEQ ID NO: 9) |
| | 8-2F | GGATCCTAATACGACTCACTATAGGGAGCCACCATGGACTA TAAAGACGACGAC (SEQ ID NO: 10) |
| | 8-2R | TTAAATGTATACCCAAAGACAAAAG (SEQ ID NO: 9) |
| 9 | 9-1F | GGACTATAAAGACGACGACGACAAAACCTGCACGACTCCT GCTCAA (SEQ ID NO: 16) |
| | 9-1R | TTAAATGTATACCCAAAGACAAAAG (SEQ ID NO: 9) |
| | 9-2F | GGATCCTATTTAGGTGACACTATAGGAGCCACCATGGACTA TAAAGACGACG (SEQ ID NO: 17) |
| | 9-2R | TTAAATGTATACCCAAAGACAAAAG (SEQ ID NO: 9) |

Successful detection of three different HBV C-terminal truncation mutants (DNA derived from the stable clone cell lines) by TRANSCEND™ chemiluminescent detection system are shown in FIG. 8. The signals were strong, and the protein sizes of all 3 mutants are all correct.

The test was also conducted on HCC tissue samples (500 ng) from 4 HBV patients (FIG. 9). Different truncation mutations were identified successfully. The intensity was directly correlated with the amount of mutant in the liver tissue.

In summary, we have identified a small percentage of HCCs with positive staining of HBcAg in the tumor tissue by IHC staining. Since the results usually suggested active replication of HBV, we performed southern blot analyses and confirmed the presence of freely replicating HBV in cancerous tissues, which was rarely known before. Because of the presence of freely replicative HBV in the cancerous tissues and the smaller size of these HBcAg-positive tumors, it was believed that these tissues might preserve HBV mutants that contribute to the early stage of hepatocarcinogenesis. The oncogenic activity of the three S gene C-terminal truncation mutants (L95, L216 and W182) was demonstrated by the xenograft study and in vivo migration assay. Among them, W182 was found to have the most potent oncogenic activity. In addition, another 4 different HBV S truncation mutants with transformation activities were also found. The above results would suggest that most of the S gene truncation mutations have transformation activity. The clinical analyses revealed that sW182'-positive patients were significantly associated with small tumor size (≤2 cm) and more commonly found in early pathological stage, which is consistent with our assumption that oncogenic viral mutants could be associated with early carcinogenesis. Thus, screening of specific HBV S gene truncation mutants in chronic hepatitis B patients will help in prediction or early diagnosis of HCC. Since direct sequencing of HBV gene is quite difficult due to the complexity of the mutations and co-existence of multiple mutations, the present invention is useful for detection of all of the C-terminal truncation mutations of HBV S gene in one test.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method for in vitro detection of the presence of a C-terminal truncation mutation of a hepatitis B virus (HBV) surface (S) gene encoding a small S protein in an isolated nucleic acid sample, comprising:
   a) providing a first set of primer pair and a second set of primer pair, the first set of primer pair comprising a first forward primer and a reverse primer, the second set of primer pair comprising a second forward primer and the reverse primer, wherein
      i) the first forward primer of the first set of primer pair comprises a nucleotide sequence selected from the group consisting of SEQ ID NOs: 8, 11, 13, 14, and 16;
      ii) the second forward primer of the second set of primer pair comprises a nucleotide sequence selected from the group consisting of SEQ ID NOs: 10, 12, 15 and 17; and
      iii) the reverse primer comprises the nucleotide sequence of SEQ ID NO: 9,
   b) performing a first PCR in a first reaction mixture comprising the isolated nucleic acid sample and the first set of primer pair to generate the first PCR product, wherein the isolated nucleic acid sample is from an HBV carrier or a suspect of HBV carrier;
   c) performing a second PCR in a second reaction mixture comprising the first PCR product and the second set of primer pair to generate the second PCR product;
   d) translating the second PCR product into a protein;
   e) comparing the size of the protein with the size of a control or wild-type small S protein; and
   f) determining that the C-terminal truncation mutation of the hepatitis B virus S gene is present in the nucleic acid sample when there is a decrease in the size of the protein as compared with the control or wild type small S protein.

2. The method of claim 1, wherein the C-terminal truncation mutation of the HBV S gene is selected from the group consisting of sL15*, sL21*, sS61*, sC69*, sL95*, sW156*, sW163*, sW172*, sW182*, sW196*, and sL216*.

3. The method of claim 1, wherein the nucleic acid sample is obtained from a patient who is suspected of having a hepatitis B virus (HBV) infection or hepatocellular carcinoma, or has an abnormal liver function or has liver cirrhosis.

4. The method of claim 1, wherein the nucleic acid sample is extracted from a fresh frozen liver tissue or a formalin-fixed paraffin tissue section, or a blood sample.

5. The method of claim 1, wherein the first PCR product spans the sequence of the HBV S gene for encoding the small S protein at least from the amino acid position 123 to the amino acid position 227 of SEQ ID NO: 2 and is labeled with a FLAG tag sequence at the 5'-end thereof.

6. The method of claim 1, wherein the first PCR product spans the sequence of the HBV S gene encoding the small S protein from the amino acid position 30 to the amino acid position 227 of SEQ ID NO: 2, or from the amino acid position 123 to the amino acid position 227 of SEQ ID NO: 2.

7. The method of claim 1, wherein the first forward primer and the second forward primer comprise nucleotide sequences respectively selected from the group consisting of:
 (a) SEQ ID NOs: 8 and 10;
 (b) SEQ ID NOs: 11 and 12;
 (c) SEQ ID NOs: 8 and 12;
 (d) SEQ ID NOs: 13 and 12;
 (e) SEQ ID NOs: 13 and 10;
 (f) SEQ ID NOs: 14 and 12;
 (g) SEQ ID NOs: 14 and 15;
 (h) SEQ ID NOs: 14 and 10; and
 (i) SEQ ID NOs: 16 and 17.

8. The method of claim 1, wherein the sequence of the first forward primer is SEQ ID NOs: 14, and the sequence of the second forward primer is SEQ ID NO: 15.

9. A method for in vitro detection of at least one C-terminal truncation mutation of a hepatitis B virus (HBV) surface (S) gene in a nucleic acid sample, comprising:
 a) providing a first forward primer and a reverse primer, the first forward primer comprising a sequence for annealing to the 5'-end of the S gene and having a FLAG tag sequence at the 5'-end thereof, the reverse primer comprising a nucleotide sequence for annealing to the 3'-end of the S gene, the first forward primer consisting of a nucleotide sequence selected from the group consisting of SEQ ID NOs: 8, 11, 13, 14, and 16, and the reverse primer consisting of the nucleotide sequence of SEQ ID NO: 9;
 b) performing a first polymerase chain reaction (PCR) in a first reaction mixture comprising the nucleic acid sample, the first forward primer, and the reverse primer to generate a first PCR product, the first PCR product comprising the FLAG tag sequence at the 5'-end thereof, wherein the nucleic acid sample is from a human subject who is a carrier of HBV or a suspect of HBV carrier;
 c) providing a second forward primer and the reverse primer, the second forward primer consisting of a nucleotide sequence selected from the group consisting of SEQ ID NOs: 10, 12, 15 and 17;
 d) performing a second PCR in a second reaction mixture comprising the first PCR product, the second forward primer, and the reverse primer to generate a second PCR product, the second PCR product comprising the T7 or the Sp6 promoter sequence at the 5'-end thereof the Kozak sequence, the FLAG tag sequence, the Kozak sequence being located between the T7 or the Sp6 promoter sequence and the FLAG tag sequence;
 e) translating the second PCR product into a protein;
 f) comparing the size of the second PCR product with the size of a wild-type small S protein; and
 (g) determining that the C-terminal truncation mutation of the hepatitis B virus S gene is present in the nucleic acid sample when the size of the protein is smaller than that of the wild-type small S protein.

10. An in vitro diagnostic kit for use in detecting the presence of a C-terminal truncation mutation of a hepatitis B virus (HBV) surface (S) gene in a nucleic acid sample according to the method of claim 1, said in vitro diagnostic kit comprising:
 (a) a first set of primer pair, which have characteristics of annealing to the HBV S gene in the nucleic acid sample in a first polymerase chain reaction (PCR) for generating a first polymerase chain reaction (PCR) product, the first PCR product spanning the sequence of the HBV S gene for encoding a small S protein at least from the amino acid position 123 to the amino acid position 227 of SEQ ID NO: 2 and is labeled with a FLAG tag sequence at the 5'-end thereof; and
 (b) a second set of primer pair, which have characteristics of annealing to the first PCR product in a second PCR for generating a second PCR product, the second PCR product spanning the sequence of the first PCR product;
 wherein
 a) the first forward primer of the first set of primer pair consists of a nucleotide sequence selected from the group consisting of SEQ ID NOs: 8, 11, 13, 14, and 16;
 b) the second forward primer of the second set of primer pair consists of a nucleotide sequence selected from the group consisting of SEQ ID NOs: 10, 12, 15 and 17; and
 c) the reverse primer consists of the nucleotide sequence of SEQ ID NO: 9.

11. The in vitro diagnostic kit of claim 10, wherein the first PCR product spans the sequence of the HBV S gene encoding small S protein from the amino acid position 30 to the amino acid position 227 of SEQ ID NO: 2, or from the amino acid position 123 to the amino acid position 227 of SEQ ID NO: 2.

12. The method of claim 1, wherein the comparing step is performed by a Western blot or a chemiluminescent detection system.

13. The method of claim 9, wherein the comparing step is performed by a Western blot or a chemiluminescent detection system.

\* \* \* \* \*

SEQUENCE LISTING

```
<160> NUMBER OF SEQ ID NOS: 17

<210> SEQ ID NO 1
<211> LENGTH: 681
<212> TYPE: DNA
<213> ORGANISM: Hepatitis B virus

<400> SEQUENCE: 1
atggagaaca tcgcatcagg actcctagga cccctgctcg tgttacaggc ggggttttc      60 ttgttgacaa aaatcctcac aataccacag agtctagact cgtggtggac ttctctcaat     120
tttctagggg gaacacccgt gtgtcttggc caaaattcgc agtcccaaat ctccagtcac    180
tcaccaacct gttgtcctcc aatttgtcct ggttatcgct ggatgtgtct gcggcgtttt    240
atcatcttcc tctgcatcct gctgctatgc ctcatcttct tgttggttct tctggactat    300
caaggtatgt tgcccgtttg tcctctaatt ccaggatcat caacaaccag caccggacca    360
tgcaaaacct gcacaactcc tgctcaagga acctctatgt ttccctcatg ttgctgtaca    420
aaacctacgg acggaaactg cacctgtatt cccatcccat catcttggc  tttcgcaaaa    480 tacctatggg agtgggcctc agtccgtttc tcttggctca gtttactagt gccatttgtt    540
cagtggttcg tagggctttc ccccactgtc tggctttcag ttatatggat gatgtggtat    600
tgggggccaa gtctgtacaa catcttgagt cccttatgc  cgctgttacc aatttttcttt    660 tgtctttggg tatacatttg a                                              681

<210> SEQ ID NO 2
<211> LENGTH: 226
<212> TYPE: PRT
<213> ORGANISM: Hepatitis B virus

<400> SEQUENCE: 2

Met Glu Asn Ile Ala Ser Gly Leu Leu Gly Pro Leu Leu Val Leu Gln
1               5                   10                  15

Ala Gly Phe Phe Leu Leu Thr Lys Ile Leu Thr Ile Pro Gln Ser Leu
            20                  25                  30

Asp Ser Trp Trp Thr Ser Leu Asn Phe Leu Gly Gly Thr Pro Val Cys
        35                  40                  45

Leu Gly Gln Asn Ser Gln Ser Gln Ile Ser Ser His Ser Pro Thr Cys
```

```
                50                  55                  60
Cys Pro Pro Ile Cys Pro Gly Tyr Arg Trp Met Cys Leu Arg Arg Phe
 65                  70                  75                  80

Ile Ile Phe Leu Cys Ile Leu Leu Cys Leu Ile Phe Leu Leu Val
             85                   90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Lys Cys Thr Thr Pro Ala
            115                 120                 125

Gln Gly Thr Ser Met Phe Pro Ser Cys Cys Thr Lys Pro Thr Asp
            130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Asn Ile
            195                 200                 205

Leu Ser Pro Phe Met Pro Leu Leu Pro Ile Phe Phe Cys Leu Trp Val
            210                 215                 220

Tyr Ile
225

<210> SEQ ID NO 3
<211> LENGTH: 19
<212> TYPE: DNA
<213> ORGANISM: Artificial Sequence
<220> FEATURE:
<223> OTHER INFORMATION: T7 promoter

<400> SEQUENCE: 3
taatacgact cactatagg                                                  19

<210> SEQ ID NO 4
<211> LENGTH: 19
<212> TYPE: DNA
<213> ORGANISM: Artificial Sequence
<220> FEATURE:
<223> OTHER INFORMATION: Sp6 promoter

<400> SEQUENCE: 4
tatttaggtg acactatag                                                  19

<210> SEQ ID NO 5
<211> LENGTH: 11
<212> TYPE: DNA
<213> ORGANISM: Artificial Sequence
<220> FEATURE:
<223> OTHER INFORMATION: Kozak consensus sequence with a short spacer

<400> SEQUENCE: 5
gagccaccat g                                                          11

<210> SEQ ID NO 6
<211> LENGTH: 13
<212> TYPE: DNA
<213> ORGANISM: Artificial Sequence
<220> FEATURE:
<223> OTHER INFORMATION: Kozak consensus sequence with a long spacer
```

```
<400> SEQUENCE: 6
aacagccacc atg                                                        13

<210> SEQ ID NO 7
<211> LENGTH: 24
<212> TYPE: DNA
<213> ORGANISM: Artificial Sequence
<220> FEATURE:
<223> OTHER INFORMATION: FLAG

<400> SEQUENCE: 7
gactataaag acgacgacga caaa                                            24

<210> SEQ ID NO 8
<211> LENGTH: 48
<212> TYPE: DNA
<213> ORGANISM: Artificial Sequence
<220> FEATURE:
<223> OTHER INFORMATION: 1-1F primer

<400> SEQUENCE: 8
atggactata aagacgacga cgacaaaacc tgcacgactc ctgctcaa                  48

<210> SEQ ID NO 9
<211> LENGTH: 25
<212> TYPE: DNA
<213> ORGANISM: Artificial Sequence
<220> FEATURE:
<223> OTHER INFORMATION: Reverse Primer 1-1R

<400> SEQUENCE: 9
ttaaatgtat acccaaagac aaaag                                           25

<210> SEQ ID NO 10
<211> LENGTH: 54
<212> TYPE: DNA
<213> ORGANISM: Artificial Sequence
<220> FEATURE:
<223> OTHER INFORMATION: Forward primer 1-2F

<400> SEQUENCE: 10
ggatcctaat acgactcact atagggagcc accatggact ataaagacga cgac           54

<210> SEQ ID NO 11
<211> LENGTH: 50
<212> TYPE: DNA
<213> ORGANISM: Artificial Sequence
<220> FEATURE:
<223> OTHER INFORMATION: Forward primer 2-1F

<400> SEQUENCE: 11
ccatggacta taaagacgac gacgacaaaa cctgcacgac tcctgctcaa                50

<210> SEQ ID NO 12
<211> LENGTH: 54
<212> TYPE: DNA
<213> ORGANISM: Artificial Sequence
<220> FEATURE:
<223> OTHER INFORMATION: Forward primer 2-2F

<400> SEQUENCE: 12
ggatcctaat acgactcact ataggaacag ccaccatgga ctataaagac gacg           54

<210> SEQ ID NO 13
<211> LENGTH: 50
```

```
<212> TYPE: DNA
<213> ORGANISM: Artificial Sequence
<220> FEATURE:
<223> OTHER INFORMATION: Forward primer 4-1F

<400> SEQUENCE: 13
ccatggacta taaagacgac gacgacaaac agagtctaga ctcgtggtgg            50

<210> SEQ ID NO 14
<211> LENGTH: 46
<212> TYPE: DNA
<213> ORGANISM: Artificial Sequence
<220> FEATURE:
<223> OTHER INFORMATION: Forward primer 6-1F

<400> SEQUENCE: 14
ggactataaa gacgacgacg acaaacagag tctagactcg tggtgg                46

<210> SEQ ID NO 15
<211> LENGTH: 55
<212> TYPE: DNA
<213> ORGANISM: Artificial Sequence
<220> FEATURE:
<223> OTHER INFORMATION: forward primer 7-2F

<400> SEQUENCE: 15
ggatcctatt taggtgacac tatagaacag accaccatgg actataaaga cgacg      55

<210> SEQ ID NO 16
<211> LENGTH: 46
<212> TYPE: DNA
<213> ORGANISM: Artificial Sequence
<220> FEATURE:
<223> OTHER INFORMATION: Forward primer 9-1F

<400> SEQUENCE: 16
ggactataaa gacgacgacg acaaaacctg cacgactcct gctcaa                46

<210> SEQ ID NO 17
<211> LENGTH: 53
<212> TYPE: DNA
<213> ORGANISM: Artificial Sequence
<220> FEATURE:
<223> OTHER INFORMATION: Forward primer 9-2F

<400> SEQUENCE: 17
gatcctattt aggtgacact ataggagcca ccatggacta taaagacgac gac        53
```